US011111197B2

(12) United States Patent
Fenyn et al.

(10) Patent No.: US 11,111,197 B2
(45) Date of Patent: *Sep. 7, 2021

(54) PROCESS FOR THE PREPARATION OF ALPHA, BETA UNSATURATED ALDEHYDES BY OXIDATION OF ALCOHOLS IN THE PRESENCE OF A LIQUID PHASE (71) Applicant: BASF SE, Ludwigshafen am Rhein (DE)

(72) Inventors: Michaela Fenyn, Ludwigshafen am Rhein (DE); Joseph John Zakzeski, Ludwigshafen am Rhein (DE); Nicolas Vautravers, Ludwigshafen am Rhein (DE); Joaquim Henrique Teles, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/956,972

(22) PCT Filed: Dec. 5, 2018

(86) PCT No.: PCT/EP2018/083623
§ 371 (c)(1),
(2) Date: Jun. 22, 2020

(87) PCT Pub. No.: WO2019/121012
PCT Pub. Date: Jun. 27, 2019

(65) Prior Publication Data
US 2020/0392060 A1 Dec. 17, 2020

(30) Foreign Application Priority Data
Dec. 21, 2017 (EP) .................... 17209517

(51) Int. Cl.
*C07C 45/38* (2006.01)
*B01J 23/42* (2006.01)
*B01J 23/44* (2006.01)
*B01J 23/52* (2006.01)
*C07C 47/21* (2006.01)

(52) U.S. Cl.
CPC .............. *C07C 45/38* (2013.01); *B01J 23/42* (2013.01); *B01J 23/44* (2013.01); *B01J 23/52* (2013.01); *C07C 47/21* (2013.01)

(58) Field of Classification Search
CPC ........... C07C 45/38; C07C 45/39; B01J 23/42
See application file for complete search history.

(56) References Cited

U.S. PATENT DOCUMENTS

| 4,165,342 A * | 8/1979 | Dudeck | C07C 45/38 |
| | | | 568/450 |
| 6,013,843 A * | 1/2000 | Aquila | B01J 8/0242 |
| | | | 568/450 |
| 6,476,260 B1 * | 11/2002 | Herrmann | C07C 45/84 |
| | | | 562/538 |
| 9,969,708 B2 * | 5/2018 | Vautravers | C07D 317/36 |
| 9,975,837 B2 * | 5/2018 | Schelwies | C07C 45/62 |
| 10,087,395 B2 * | 10/2018 | Pelzer | C07C 45/82 |
| 10,112,882 B2 * | 10/2018 | Thrun | C07C 45/29 |
| 10,144,691 B2 * | 12/2018 | Vautravers | C07C 45/82 |
| 10,195,598 B2 * | 2/2019 | Riedel | B01J 38/48 |
| 10,202,324 B2 * | 2/2019 | Vautravers | C07C 45/78 |
| 10,259,822 B2 * | 4/2019 | Werner | C07D 493/06 |

FOREIGN PATENT DOCUMENTS

| EP | 0881206 A1 | 12/1998 |
| JP | 2010-202555 A | 9/2010 |
| WO | 99/18058 A1 | 4/1999 |
| WO | 2008/037693 A1 | 4/2008 |
| WO | 2018/002040 A1 | 1/2018 |

OTHER PUBLICATIONS

Anderson et al., "Selective Oxidation of Alcohols to Carbonyl Compounds and Carboxylic Acids with Platinum Group Metal Catalysts", Adv. Synth. Catal., vol. 345, 2003, pp. 517-523.
Besson et al., "Selective oxidation of alcohols and aldehydes on metal catalysts", Catalysis Today, vol. 57, 2000, pp. 127-141.
Hau-ng et al., "An efficient and reusable carbon-supported platinum catalyst for aerobic oxidation of alcohols in water", Chem. Commun., 2008, pp. 3181-3183.
Heyns et al., "Katalytische oxydation von primären und sekundären hydroxylverbindungen mit sauerstoff am platinkontakt in flüssiger phase : Über katalytische oxydationen—XIV", Tetrahedron, vol. 9, 1960, pp. 67-75.
International Preliminary Report on Patentability received for PCT Patent Application No. PCT/EP2018/083623, dated Jul. 2, 2020, 8 pages.
International Search Report and Written Opinion received for PCT Patent Application No. PCT/EP2018/083623, dated Feb. 11, 2019, 10 pages.
Kon et al., "Oxidation of allylic alcohols to α,β-unsaturated carbonyl compounds with aqueous hydrogen peroxide under organic solvent-free conditions", Chem. Commun., 2007, pp. 4399-4400.
Korovchenko et al: "Oxidation of primary alcohols with air on carbon-supported platinum catalysts for the synthesis of aldehydes or acids", Catalysis T, Elsevier, Amsterdam, NL, vol. 121, No. 1-2, Feb. 13, 2007 (Feb. 13, 2007), pp. 13-21.
Lee, et al., "Aspects of allylic alcohol oxidation-a bimetallic heterogeneous selective oxidation catalyst", Green Chemistry, vol. 2, Issue 6, 2000, pp. 279-282.
Wang et al., "Aqueous-phase aerobic oxidation of alcohols by soluble Pt nanoclusters in the absence of base", Chem. Commun., 2007, pp. 4375-4377.

\* cited by examiner

*Primary Examiner* — Sikarl A Witherspoon
(74) *Attorney, Agent, or Firm* — Faegre Drinker Biddle & Reath LLP (57) ABSTRACT

Process for the preparation of alpha, beta unsaturated aldehydes by oxidation of alcohols in the presence of a liquid phase.

23 Claims, 1 Drawing Sheet

Figure 1

BSE

Figure 2

PROCESS FOR THE PREPARATION OF ALPHA, BETA UNSATURATED ALDEHYDES BY OXIDATION OF ALCOHOLS IN THE PRESENCE OF A LIQUID PHASE

CROSS-REFERENCE TO RELATED APPLICATIONS

This application is a national stage application (under 35 U.S.C. § 371) of PCT/EP2018/083623, filed Dec. 5, 2018, which claims benefit of European Application No. 17209517.6, filed Dec. 21, 2017, both of which are incorporated herein by reference in their entirety.

The present invention relates to a process for preparing alpha, beta unsaturated aldehydes, such as in particular, prenal (3-methyl-2-butenal) by oxidation of alcohols in the presence of a liquid phase. More specifically, the invention relates to a process for preparing alpha, beta unsaturated aldehydes, such as, in particular prenal (3-methyl-2-butenal) by oxidation of alcohols in the presence of a liquid phase and a catalyst, wherein the liquid phase contains at least 25 weight-% water based on the total weight of the liquid phase and the oxidant is oxygen and wherein the catalyst comprises a catalytically active metal on a support.

TECHNICAL BACKGROUND

Prenal is an important chemical intermediate especially for the preparation of terpene-based fragrances, such as citral, and for the preparation of vitamins, such as vitamin E, and therefore is of great technical and economic importance.

The most common procedures for preparing prenal use prenol (3-methyl-2-buten-1-ol) or isoprenol (3-methyl-3-buten-1-ol) as starting compounds. Thus, EP 0 881 206 describes the oxidation of these starting compounds with oxygen in the gas phase using a silver catalyst. The selectivity of this approach could be improved by further developing the catalytic system, as disclosed e.g. in WO 2008/037693. However, in order to obtain sufficient conversion rates and selectivity it is necessary to carry out the gas phase procedure at temperatures of about 360° C. while maintaining short contact times. This is required, on the one hand, to ensure adequate reactivity and, on the other hand, to prevent decomposition reactions of the sensitive reactants and products. These conditions can only be accomplished by using expensive equipment.

Processes for preparing alpha, beta unsaturated aldehydes by oxidation in the liquid phase using organic solvents are disclosed in Tetrahedron, Vol 9 (1960), 67-75, Adv. Synth. Catal. 345 (2003), 517-523 as well as in Green Chemistry, 2 (2000), 279-282.

Chem. Commun. (2008), 3181-3183, describes the oxidation of benzylalcohol and cinnamylalcohol with oxygen in water. Catalysis Today 121 (2007), 13-21 describes the oxidation of substituted benzyl alcohols with oxygen. Chem. Commun. (2007), 4375-4377 discloses the oxidation of cinnamyl alcohol to cinnamic acid as well as the oxidation of benzyl alcohol to benzoic acid in the presence of water and oxygen. Catalysis Today 57 (2000) 127-141 describes the oxidation of 5-hydroxymethylfurfural as well as the oxidation of cinnamyl alcohol. JP 2010-202555A describes the oxidation of 3 groups of alcohols to the corresponding aldehydes in a liquid phase with oxygen as oxidant. None of these references discloses a process for the preparation of the alpha, beta unsaturated aldehydes according to the present invention.

WO 99/18058 discloses a process for the aerobic oxidation of primary alcohols, such as hexanol in the absence of solvents.

Chem. Commun. (2007) 4399-4400 describes the formation of alpha, beta unsaturated aldehydes in high yields with aqueous hydrogen peroxide as the oxidant in the presence of Pt black catalyst under organic solvent free conditions. Table 1 discloses this reaction for a list of alcohols: Entry 7 discloses the oxidation of 3-methyl-2-butenol to 3-methyl-2-butenal with 5% hydrogen peroxide as oxidant and Pt black as catalyst. 3-methyl-2-butenal is obtained with a yield of 91%. Entry 4 discloses this reaction for cinnamyl alcohol. On page 4399, left column this document expressly states the necessity of using hydrogen peroxide as oxidant: "Without the use of $H_2O_2$ (under an air atmosphere), cinnamaldeyde was obtained in only<10% yield." In footnote 12, this reference summarizes previous work: "Although the oxidation of cinnamyl alcohol to cinnamaldehyde with $O_2$ (or air) has been reported, organic solvents and/or base are necessary to achieve high yield and selectivity."

Chem. Commun. (2007) 4399-4400 is considered the closest prior art, as it discloses a process for the preparation of prenal from prenol by oxidation with aqueous hydrogen peroxide as oxidant in an aqueous liquid phase in the presence of a catalyst with a yield of 91%. It has to be noted that this reference explicitly discourages from using oxygen or air as oxidant in a process for preparing alpha, beta unsaturated aldehydes.

It was an objective of the invention to provide a simple and efficient process for preparing alpha, beta unsaturated aldehydes of formula (I), in particular prenal, which is suitable for industrial scale preparations. The process should be easy to handle, asure high yields and high selectivity of the aldehyde to be prepared, thus avoiding over-oxidation to the corresponding acid. Moreover, the use of toxic or expensive reagents should be avoided. Moreover, the process should allow high space-time-yields (STY), which are of major importance for the economic suitability in industrial scale processes. The space-time-yield (STY) is defined as the amount of product obtained per reaction volume per hour of reaction, expressed as g/l/h. The reaction volume is the volume of the reactor in which the reaction takes place. In case the reaction is conducted in a cylindrical reactor, the reaction volume is the volume of the cylindrical reactor in which the reaction takes place. Of special interest are processes which allow high space-time-yields in a reaction time, in which at least 40%, preferably at least 50% conversion is achieved. Furthermore, it was desired to provide a process which enables easy recovery of the aldehyde.

Moreover, the process should allow a high specific activity (SA), which is of major importance for the economic suitability in industrial scale processes. The specific activity (SA) is defined as the amount of product obtained per amount of catalytically active metal per hour of reaction, expressed as g/g/h. Of special interest are processes which allow high specific activities in a reaction time, in which at least 40%, preferably at least 50% conversion is achieved.

SUMMARY OF THE INVENTION

It has now been found that this objective is achieved by an oxidation in the presence of a catalyst and in the presence of a liquid phase, wherein the liquid phase contains at least 25 weight-% of water based on the total weight of the liquid phase, determined at 20° C. and 1 bar, and wherein oxygen is used as the oxidant and wherein the catalyst comprises a catalytically active metal on a support.

It has surprisingly been found that the alpha, beta unsaturated aldehydes of formula (I) can be obtained with excellent yield and selectivity with the process according to the invention. The process according to the invention is further associated with a series of advantages. The process according to the invention enables the preparation of alpha, beta unsaturated aldehydes of formula (I) with high yield under mild conditions, both of temperature and pressure, while requiring only moderate to low amounts of catalyst. The process can be conducted with no or low amounts of organic solvent, thus avoiding or minimizing environmentally problematic waste streams. The process also allows a simple isolation of the desired aldehyde. With the process according to the invention specific activities can be achieved, which are higher than the specific activities that are possible with processes according to the prior art.

In contrast to the process described in Chem. Commun. (2007) 4399-4400, no hydrogen peroxide needs to be employed and at the same time an increase in yield is obtained.

Therefore, the present invention relates to a process for the preparation of alpha, beta unsaturated aldehydes of general formula (I)

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

(II)

wherein $R_1$, $R_2$ and $R_3$ have the meaning as given above in the presence of a catalyst and in the presence of a liquid phase,
  wherein the liquid phase contains at least 25 weight-% water based on the total weight of the liquid phase, determined at a temperature of 20° C. and a pressure of 1 bar and
  wherein the oxidant is oxygen, and
  wherein the catalyst comprises a catalytically active metal on a support and the catalytically active metal is located mainly in the outer shell of the catalyst.

Therefore, the present invention relates to a process for the preparation of alpha, beta unsaturated aldehydes of general formula (I)

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

(II)

wherein $R_1$, $R_2$ and $R_3$ have the meaning as given above in the presence of a catalyst and in the presence of a liquid phase,
  wherein the liquid phase contains at least 25 weight-% water based on the total weight of the liquid phase, determined at a temperature of 20° C. and a pressure of 1 bar and
  wherein the oxidant is oxygen, and
  wherein a catalyst is used which is obtainable by
    a) providing a support
    b) providing a metal compound
    c) depositing the metal compound on the support
    d) optionally calcinating the so obtained catalyst precursor
    e) reducing the catalyst precursor, preferably by treatment of the catalyst precursor with a solution of a reducing agent
    f) optionally recovering the catalyst.

A BRIEF DESCRIPTION OF THE FIGURES

FIG. 2: The Y-axis shows the local Pt-concentration in weight % measured by EDX, while the X-axis shows the position at which the measurement was taken. The distances are taken along the dotted line in FIG. 1 and the zero point is at the left side.

GENERAL DEFINITIONS

Figure 1:
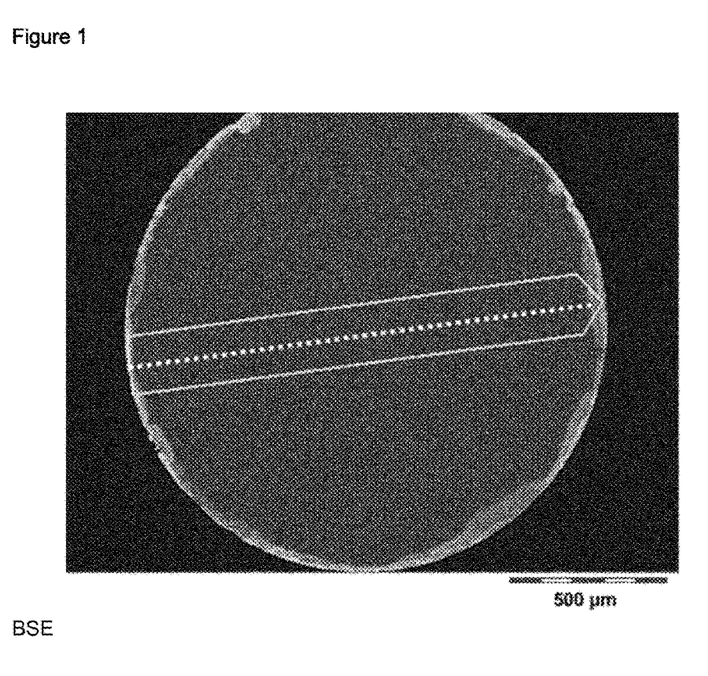
FIG. 1 and FIG. 2 display the Pt distribution in the catalyst of example C6.
Figure 2:
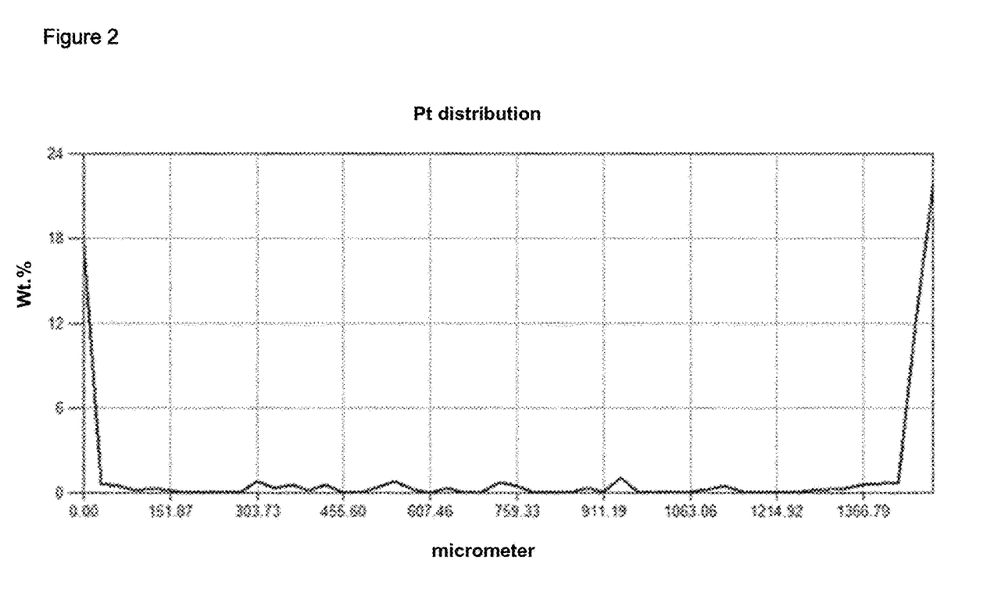

In the context of the present invention, the terms used generically are, unless otherwise stated, defined as follows:

The prefix $C_x$-$C_y$ denotes the number of possible carbon atoms in the particular case.

Alkyl and also all alkyl moieties in radicals derived therefrom, such as e.g. alkoxy, acyl, acyloxy, refers to saturated, straight-chain or branched hydrocarbon radicals having x to y carbon atoms, as denoted in $C_x$-$C_y$.

Thus, the term $C_1$-$C_4$-alkyl denotes a linear or branched alkyl radical comprising from 1 to 4 carbon atoms, such as methyl, ethyl, propyl, 1-methylethyl (isopropyl), butyl, 1-methylpropyl (sec-butyl), 2-methylpropyl (isobutyl) or 1,1-dimethylethyl (tert-butyl).

The term $C_1$-$C_6$-alkyl denotes a linear or branched alkyl radical comprising 1 to 6 carbon atoms, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

The term alkenyl denotes mono- or poly-, in particular monounsaturated, straight-chain or branched hydrocarbon radicals having x to y carbon atoms, as denoted in $C_x$-$C_y$, and a double bond in any desired position, e.g. $C_1$-$C_6$-alkenyl, preferably $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

The term substituents denotes radicals selected from the group consisting of $NO_2$, CN, halogen, $C_1$-$C_6$ alkoxy, ($C_1$-$C_6$-alkoxy)carbonyl, $C_1$-$C_6$ acyl, $C_1$-$C_6$ acyloxy and aryl.

The term halogen denotes in each case fluorine, bromine, chlorine or iodine, especially fluorine, chlorine or bromine.

The term alkoxy denotes straight-chain or branched saturated alkyl radicals comprising from 1 to 6 ($C_1$-$C_6$-alkoxy) or 1 to 4 ($C_1$-$C_4$-alkoxy) carbon atoms, which are bound via an oxygen atom to the remainder of the molecule, such as methoxy, ethoxy, n-propoxy, 1-methylethoxy (isopropoxy), n-butyloxy, 1-methylpropoxy (sec-butyloxy), 2-methylpropoxy (isobutyloxy) and 1,1-dimethylethoxy (tert-butyloxy).

The term ($C_1$-$C_6$-alkoxy)carbonyl denotes alkoxy radicals having from 1 to 6 carbon atoms which are bound via a carbonyl group to the remainder of the molecule. Examples thereof are methoxycarbonyl, ethoxycarbonyl, propoxycarbonyl, isopropoxycarbonyl, n-butoxycarbonyl, secbutoxycarbonyl, isobutoxycarbonyl and tert-butoxycarbonyl, n-pentyloxycarbonyl and n-hex-yloxycarbonyl.

The term $C_1$-$C_6$ acyl denotes straight-chain or branched saturated alkyl radicals comprising from 1 to 6 carbon atoms, which are bound via a carbonyl group to the remainder of the molecule. Examples thereof are formyl, acetyl, propionyl, 2-methylpropionyl, 3-methylbutanoyl, butanoyl, pentanoyl, hexanoyl.

The term $C_1$-$C_6$ acyloxy denotes $C_1$-$C_6$ acyl radicals, which are bound via an oxygen atom to the remainder of the molecule. Examples thereof are acetoxy, propionyloxy, butanoyloxy, pentanoyloxy, hexanoyloxy.

The term aryl denotes carbocyclic aromatic radicals having from 6 to 14 carbon atoms. Examples thereof comprise phenyl, naphthyl, fluorenyl, azulenyl, anthracenyl and phenanthrenyl. Aryl is preferably phenyl or naphthyl, and especially phenyl.

Selectivity is defined as the number of moles of the alpha, beta unsaturated aldehyde of the general formula (I) formed divided by the number of moles of the alcohol of the general formula (II) that were consumed. The amounts of alpha, beta unsaturated aldehyde of the general formula (I) formed and of alcohol of the general formula (II) consumed can easily be determined by a GC analysis as defined in the experimental section.

The terms "conducted" and "performed" are used synonymously.

PREFERRED EMBODIMENT OF THE INVENTION

The remarks made below regarding preferred embodiments of the reactant(s) and product(s) and the process according to the invention, especially regarding preferred meanings of the variables of the different reactant(s) and product(s) and of the reaction conditions of the process, apply either taken alone or, more particularly, in any conceivable combination with one another.

Alcohol(s) of General Formula (II)

Reactant(s) of the process of the invention are alcohol(s) of general formula (II)

(II)

wherein $R_1$, $R_2$ and $R_3$, independently of one another, are selected from hydrogen;

$C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy)carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy)carbonyl, $C_1$-$C_6$ acyl, $C_1$-$C_6$ acyloxy and aryl;

The terms "reactant(s)" and "alcohol(s) of general formula (II)" are used synonymously. The term alcohol(s) encompasses one alcohol as well as a mixture of more than one alcohol according to formula (II).

In one embodiment of the invention alcohol(s) of general formula (II) are used, wherein $R_3$ is H.

In one embodiment of the invention alcohol(s) of general formula (II) are used, wherein $R_1$, $R_2$ and $R_3$, independently of one another, are selected from the group consisting of H, $C_1$-$C_6$-alkyl and $C_2$-$C_6$-alkenyl.

In one embodiment of the invention alcohol(s) of general formula (II) are used, wherein $R_1$, $R_2$ and $R_3$, independently of one another, are selected from the group consisting of H, $C_1$-$C_6$-alkyl and $C_2$-$C_4$-alkenyl.

In one embodiment of the invention alcohol(s) of general formula (II) are used, wherein $R_1$, $R_2$ and $R_3$, independently of one another, are selected from the group consisting of H, $C_1$-$C_4$-alkyl and $C_2$-$C_6$-alkenyl.

In one embodiment of the invention alcohol(s) of general formula (II) are used, wherein $R_1$, $R_2$ and $R_3$, independently of one another, are selected from the group consisting of H, $C_1$-$C_4$-alkyl and $C_2$-$C_4$-alkenyl.

In one embodiment of the invention alcohol(s) of general formula (II) are used, wherein $R_1$, $R_2$ and $R_3$, independently of one another, are selected from the group consisting of H, $CH_3$ and $C_2H_5$.

In one embodiment of the invention alcohol(s) of general formula (II) are used, wherein $R_1$, $R_2$ and $R_3$, independently of one another, are selected from the group consisting of H and $CH_3$.

In one embodiment of the invention an alcohol of the general formula (II) is used, wherein $R_1$ is H and $R_2$ and $R_3$ are $CH_3$.

In one embodiment of the invention an alcohol of the general formula (II) is used, wherein $R_3$ is H and $R_1$ and $R_2$ are $CH_3$ (=3-Methyl-2-buten-1-ol, prenol).

In one embodiment of the invention an alcohol of the general formula (II) is used, wherein $R_1$ is $CH_3$, $R_3$ is H and $R_2$ is $C_6$-Alkenyl, preferably 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl; Each double bond in the alkenyl moiety can independently of each other be present in the E- as or the Z-configuration.

In one embodiment of the invention an alcohol of the general formula (II) is used, wherein $R_2$ is $CH_3$, $R_3$ is H and $R_1$ is $C_6$-Alkenyl, preferably 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl; Each double bond in the alkenyl moiety can independently of each other be present in the E- as or the Z-configuration.

In one embodiment of the invention the alcohol of the general formula (II) is selected from the group consisting of (2E)-3,7-dimethylocta-2,6-dien-1-ol, (2Z)-3,7-dimethylocta-2,6-dien-1-ol, 3-methylbut-2-en-1-ol, (E)-2-methylbut-2-en-1-ol and (Z)-2-methylbut-2-en-1-ol.

In one embodiment of the invention the alcohol of the general formula (II) is 3-methylbut-2-en-1-ol. In case the alcohol of general formula (II) is 3-methylbut-2-en-1-ol, the invention also encompasses the embodiment that 2-methyl-3-buten-2-ol (dimethylvinylcarbinol, DMVC) is added to the reaction and subsequently isomerized to 3-methylbut-2-en-1-ol.

In one embodiment of the invention the alcohol of the general formula (II) is a mixture of (2E)-3,7-dimethylocta-2,6-dien-1-ol and (2Z)-3,7-dimethylocta-2,6-dien-1-ol.

Alpha, Beta Unsaturated Aldehyde(s) of General Formula (I)

Product(s) of the process of the invention are alpha, beta unsaturated aldehyde(s) of general formula (I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy)carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy)carbonyl, $C_1$-$C_6$ acyl, $C_1$-$C_6$ acyloxy and aryl.

The terms "product(s)" and "alpha, beta unsaturated aldehyde(s) of general formula (I)" are used synonymously. The term "aldehyde(s)" encompasses one aldehyde as well as a mixture of more than one aldehyde according to formula (I).

Liquid Phase

It has surprisingly been found that the process according to the invention can be performed in the presence of a liquid phase, wherein the liquid phase contains at least 25 weight-% water based on the total weight of the liquid phase, determined at a temperature of 20° C. and a pressure of 1 bar.

The process according to the invention is conducted in the presence of a liquid phase. The liquid phase consists of all components of the reaction which are liquid at 20° C. and a pressure of 1 bar.

All weight-% of the liquid phase referred to in the process according to the invention are based on the total weight of the liquid phase, determined at a temperature of 20° C. and a pressure of 1 bar.

The process according to the invention is conducted at the interphase between liquid phase and the solid catalyst (heterogeneous catalyzed process).

The solid catalyst is not liquid at a temperature of 20° C. and a pressure of 1 bar and is therefore by definition not included in the weight-% of the liquid phase.

The liquid phase can consist of one or more, e.g. two or three distinct liquid phases. The number of liquid phases can be chosen by a man skilled in the art, dependent for example on the choice and concentration of the alcohol(s) of general formula (II) or on optional solvent(s).

The process according to the invention can be conducted in the presence of a liquid phase, which consists of one liquid phase (mono-phase system). The process according to the invention can be conducted in the presence of a liquid phase, which consists of more than one, e.g. two, three or more distinct liquid phases (multi-phase system).

In case the process according to the invention is conducted in the presence of a liquid phase which consists of one liquid phase, the liquid phase contains at least 25 weight-% water, determined at a temperature of 20° C. and a pressure of 1 bar.

In case the process according to the invention is conducted in the presence of a liquid phase which consists of more than one liquid phase, at least one distinct liquid phase contains at least 25 weight-% water, determined at a temperature of 20° C. and a pressure of 1 bar.

In one embodiment of the invention the process according to the invention can be performed in the presence of a liquid phase, which consists of two or three distinct liquid phases, wherein each distinct liquid phase contains at least 25 weight-% of water based on the total weight of this distinct liquid phase, determined at a temperature of 20° C. and a pressure of 1 bar.

The water content of a liquid phase can for example be adjusted by adding water (e.g. if a liquid phase is an aqueous phase) or by adding water and/or solvents and/or solubilizers (e.g. if a liquid phase is a non-aqueous phase, e.g. comprising reactant(s) and/or product(s) not dissolved in the aqueous phase).

The following preferred ranges for the water content of a liquid phase apply for the at least one or each distinct liquid phase accordingly.

In a preferred embodiment of the invention the process is performed in a liquid phase, which contains at least 30 weight-%, preferably at least 40 weight-%, more preferably at least 50 weight-% of water. In a further embodiment the process can be performed in a liquid phase, which contains at least 60 weight-%, preferably at least 70 weight-%, more preferably at least 80 weight-%, more preferably at least 90 weight-%, more preferably at least 95 weight-% of water. According to one embodiment of the invention, the process can be performed in a liquid phase which contains 99.5 weight-% of water. All weight-% of water are based on the total weight of the liquid phase (or the at least one or each distinct liquid phase in case more than one liquid phase is present).

In one embodiment of the invention each distinct liquid phase contains at least 25 weight-% of water based on the total weight of this distinct liquid phase. The weight-% of water are determined at a temperature of 20° C. and a pressure of 1 bar.

Solvent(s)

The process according to the invention can be carried out in the presence of a liquid phase which essentially consist of reactant(s), product(s), water and oxidant.

The process according to the invention can be carried out as a heterogeneous catalyzed process in the presence of a liquid phase which essentially consist of reactant(s), product(s), water and oxidant(s).

In these embodiments, the liquid phase contains no solvent. The term "solvent" encompasses any component other than reactant(s), product(s), water and possibly oxidant(s) or possibly catalyst(s) which is liquid at a temperature of 20° C. and a pressure of 1 bar and which is thus part of the liquid phase.

It is therefore one of the advantages of the present invention, that the process can be performed in the presence of a liquid phase, which comprises less than 75 weight-%, preferably less than 70 weight-% solvent based on the total weight of the liquid phase.

In case a solvent is employed, a suitable solvent can be selected depending on the reactant(s), product(s), catalyst(s), oxidant and reaction conditions. The term "solvent" encompasses one or more than one solvents.

The following preferred ranges for the solvent content of a liquid phase apply for the liquid phase (for mono-phase systems) or for the at least one distinct liquid phase (for multi-phase systems).

In a preferred embodiment of the invention the process is performed in a liquid phase, which contains less than 70 weight-%, preferably less than 60 weight-%, preferably less than 50 weight-%, preferably less than 40 weight-%, preferably less than 30 weight-%, more preferably less than 20 weight-%, more preferably less than 10 weight-% solvent based on the total weight of the liquid phase (for mono-phase systems) or the at least one distinct liquid phase (for multi-phase systems).

Advantageously the process according to the invention can be performed in the presence of a liquid phase, which contains less than 5 weight-% solvent based on the total weight of the liquid phase (for mono-phase systems) or the at least one distinct liquid phase (for multi-phase systems). In one embodiment of the invention the process is performed in the presence of a liquid phase which contains less than 3 weight-%, preferably less than 1 weight-% of solvent. In one embodiment of the invention the process is performed in the presence of a liquid phase which contains no solvent.

In case a solvent is employed, suitable solvents are for example protic or aprotic solvents.

In case a solvent is employed, it has been found to be advantageous to use an aprotic organic solvent for the reaction of the alcohol(s) of general formula (II).

In case a solvent is employed, solvents are preferred that have a boiling point above 50° C., for instance in the range of 50 to 200° C., in particular above 65° C., for instance in the range of 65 to 180° C., and specifically above 80° C., for instance in the range of 80 to 160° C.

Useful aprotic organic solvents here include, for example, aliphatic hydrocarbons, such as hexane, heptane, octane, nonane, decane and also petroleum ether, aromatic hydrocarbons, such as benzene, toluene, the xylenes and mesitylene, aliphatic $C_3$-$C_8$-ethers, such as 1,2-dimethoxyethane (DME), diethylene glycol dimethyl ether (diglyme), diethyl ether, dipropyl ether, methyl isobutyl ether, tert-butyl methyl ether and tert-butyl ethyl ether, dimethoxymethane, diethoxymethane, dimethylene glycol dimethyl ether, dimethylene glycol diethyl ether, trimethylene glycol dimethyl ether, trimethylene glycol diethyl ether, tetramethylene glycol dimethyl ether, cycloaliphatic hydrocarbons, such as cyclohexane and cycloheptane, alicyclic $C_3$-$C_6$-ethers, such as tetrahydrofuran (THF), tetrahydropyran, 2-methyltetrahydrofuran, 3-methyltetrahydrofuran, 1,3-dioxolane, and 1,4-dioxane, 1,3,5-trioxane, short-chain ketones, such as acetone, ethyl methyl ketone and isobutyl methyl ketone, $C_3$-$C_6$-esters such as methyl acetate, ethyl acetate, methyl propionate, dimethyloxalate, methoxyacetic acid methyl ester, ethylene carbonate, propylene carbonate, ethylene glycol diacetate and diethylene glycol diacetate, $C_3$-$C_6$-amides such as dimethylformamide (DMF) and dimethylacetamide and N-methylpyrrolidone (NMP), dimethyl sulfoxide (DMSO), $C_3$-$C_6$-nitriles such as acetonitrile, propionitrile or mixtures of these solvents with one another.

According to an embodiment of the present invention those of the aforementioned aprotic solvents are preferred that have a boiling point above 50° C., for instance in the range of 50 to 200° C., in particular above 65° C., for instance in the range of 65 to 180° C., and specifically above 80° C., for instance in the range of 80 to 160° C.

More preferably the solvent, if employed, is selected from the group consisting of 1,2-dimethoxyethane (DME), diethylene glycol dimethyl ether (diglyme), diethoxymethane, dimethylene glycol dimethyl ether, tri-methylene glycol dimethyl ether, tetramethylene glycol dimethyl ether, 1,3-dioxolane, 1,4-dioxane, 1,3,5-trioxane, dimethylacetamide, methyl acetate, dimethyloxalate, methoxyacetic acid methyl ester, ethylene carbonate, propylene carbonate, ethylene glycol diacetate and diethylene glycol diacetate, toluene, the xylenes, mesitylene, $C_7$-$C_{10}$-alkanes, such as octane or nonane, THF, 1,4-dioxane and mixtures thereof, and specifically selected from toluene, orthoxylene, meta-xylene, para-xylene and mesitylene.

In a preferred embodiment, the solvent, if employed, is selected from solvents which have a water solubility of greater 150 g/l at 20° C. In a preferred embodiment the solvent, if employed, is selected from solvents which have a vapour pressure of below 100 mbar at 20° C.

In a preferred embodiment the solvent, if employed, is selected from the group consisting of diethylene glycol dimethyl ether, triethylene glycol dimethylether and dimethylacetamide, polyoxymethylene dimethylether of general formula (III) $H_3C$—O—$(CH_2O)_n$—$CH_3$ wherein n=3 to 8, dimethyloxalate, methoxyacetic acid methyl ester, ethylene carbonate, propylene carbonate, ethylene glycol diacetate and diethylene glycol diacetate.

In a preferred embodiment of the process according to the invention, the reactant(s) and product(s) are present from 1 to less than 75 weight-%, preferably 1 to 70 weight-%, preferably 1 to 50 weight-% based on the total weight of the liquid phase, preferably from 2 to 45 weight-% based on the total weight of the liquid phase, more preferably from 3 to 40 weight-% based on the total weight of the liquid phase.

In case the liquid phase consists of more than one distinct phase, the reactant(s) and product(s) are preferably present in at least one distinct liquid phase from 1 to less than 75 weight-%, preferably from 1 to 70 weight-%, preferably 1 to 50 weight-%, preferably from 2 to 45 weight-%, more preferably from 3 to 40 weight-% based on the total weight of the at least one distinct liquid phase.

In case the liquid phase consists of more than one distinct phase, the reactant(s) and product(s) are preferably present in each distinct liquid phase from 1 to less than 75 weight-%, preferably 1 to 70 weight-%, preferably 1 to 50 weight-%, preferably from 2 to 45 weight-%, more preferably from 3 to 40 weight-% based on the total weight of each distinct liquid phase, Oxidant The process according to the invention is performed with oxygen as oxidant. Oxygen can be used undiluted or diluted. The oxygen can be diluted with other inert gases like $N_2$, Ar or $CO_2$, e.g in the form of air. In a preferred embodiment of the invention oxygen is used undiluted.

Catalyst

The process according to the invention is performed as a heterogeneous catalyzed process. In such a heterogeneous catalyzed process the catalyst and reactant(s)/product(s) are in different phases, which are in contact with each other. The reactant(s)/product(s) are in the liquid phase, whereas the catalyst will be, at least partially in a solid phase. The reaction will take place at the interphase between liquid phase and solid phase.

The process according to the invention is carried out in the presence of a catalyst, which comprises at least one catalytically active metal on a support. In the process according to the invention the catalytically active metal can be selected from the elements selected from the groups 8, 9, 10 and 11 of the periodic table (according to IUPAC nomenclature). The elements of group 8, 9, 10 and 11 of the periodic table comprise iron, cobalt, nickel, ruthenium, rhodium, palladium, osmium, iridium, platinum, copper, silver and gold.

In a preferred embodiment, the catalytically active metal is selected from elements from the groups 10 and 11 of the periodic table (according to IUPAC nomenclature).

In a preferred embodiment, the catalytically active metal is selected from elements selected from the group consisting of platinum, palladium and gold.

In a preferred embodiment of the invention the catalytically active metal is platinum.

The catalyst can optionally comprise one or more so called promotors, which enhance the activity of the catalytically active metal. Examples for such promotors are bismuth (Bi), antimony (Sb), lead (Pb), cadmium (Cd), tin (Sn), tellurium (Te), cerium (Ce), selenium (Se) or thallium (Tl).

In a preferred embodiment, the catalyst comprises at least one promotor selected from the group consisting of bismuth (Bi), antimony (Sb), lead (Pb), cadmium (Cd), tin (Sn) and tellurium (Te). In a preferred embodiment, the catalyst comprises at least one promotor selected from the group consisting of bismuth (Bi), lead (Pb) and cadmium (Cd). In a preferred embodiment, the catalyst comprises bismuth (Bi).

The promotors can for example be employed as metals, nitrates, acetates, sulphates, citrates, oxides, hydroxides or chlorides and mixtures thereof.

In a preferred embodiment, the catalytically active metal is platinum and the promotor is bismuth.

In case a promotor is employed, suitable molar ratios of the catalytically active metal and the promotor are in the range from 1:0.01 to 1:10, preferably 1:0.5 to 1:5, more preferably from 1:0.1 to 1:3.

The promotors can for example be present on the support or can be added separately to the process.

The term "on a support" encompasses that the catalytically active metal and/or promotor can be located on the outer surface of a support and/or on the inner surface of a support. In most cases, the catalytically active metal and/or promotor will be located on the outer surface of a support and on the inner surface of a support.

The catalyst comprises the catalytically active metal, the support and optionally promotors.

In one embodiment of the invention, the process is conducted as a batch process and the molar ratio of the catalytically active metal to the alcohol(s) of general formula (II) is in the range 0.0001:1 to 1:1, more preferably in the range 0.001:1 to 0.1:1 and even more preferably in the range 0.001:1 to 0.01:1.

In one embodiment of the invention, the process is conducted as a continuous process and the catalyst load (defined as total amount of alcohol of general formula (II) total amount of catalytically active metal in the reactor/time unit) is in the range 0.01 to 100 g of alcohol(s) of general formula (II) per g of catalytically active metal per hour, more preferably in the range 0.1 to 20 g of alcohol(s) of general formula (II) per g of catalytically active metal per hour.

In one embodiment of the invention, the process is conducted as a continuous process and the catalyst load (defined as total amount of alcohol of general formula (II) total amount of catalytically active metal in the reactor/time unit) is in the range 30 to 40000 g of alcohol(s) of general formula (II) per g of catalytically active metal per hour, more preferably in the range 1000 to 9000, more preferably in the range 1200 to 5000, preferably 1500 to 4000, preferably in the range of 1650 to 3500 g of alcohol(s) of general formula (II) per g of catalytically active metal per hour. The support can for example be a powder, a shaped body or a mesh, for example a mesh of iron-chromium-aluminium (FeCrAl), that was tempered in the presence of oxygen (commercially available under the trademark Kanthal®).

In a preferred embodiment, the catalytically active metal is selected from the group consisting of powders and shaped bodies. In case a support in the form of a powder is employed, such powders usually have a particle size in the range of 1 to 200 µm, preferably 1 to 100 µm. The shaped bodies can for example be obtained by extrusion, pressing or tableting and can be of any shape such as for example strands, hollow strands, cylinders, tablets, rings, spherical particles, trilobes, stars or spheres. Typical dimensions of shaped bodies range from 0.5 mm to 250 mm.

In a preferred embodiment, the support has a diameter from 0.5 to 20 mm, preferably from 0.5 to 10 mm, more preferably from 0.7 to 5 mm, more preferably from 1 to 2.5 mm, preferably 1.5 to 2.0 mm.

In a preferred embodiment, the support is obtained by extrusion and is in the form of a strand or hollow strand. In one embodiment, a support is employed with strand diameters from 1 to 10 mm, preferably 1.5 to 5 mm. In one embodiment, a support is employed with strand lengths from 2 to 250 mm, preferably 2 to 100 mm, preferably 2 to 25 mm, more preferably 5 to 10 mm. In one embodiment, a support is employed with a strand diameter of 1 to 2 mm and strand lengths of 2 to 10 mm.

In a preferred embodiment, the catalytically active metal is employed on a support, wherein the support is selected from the group consisting of carbonaceous and oxidic materials.

Suitable support materials are for example carbonaceous or oxidic materials. A preferred carbonaceous support is activated carbon. The surface area of carbonaceous support materials preferably is at least 200 m$^2$/g, preferably at least 300 m$^2$/g. In case a carbonaceous support is used an activated carbon with a surface area of at least 300 m$^2$/g is preferred. In a preferred embodiment, the catalytically active metal (preferably platinum) is employed on an activated carbon support, preferably with an activated carbon support with a surface area of at least 300 m$^2$/g.

In case an oxidic support is used, the oxides of the following elements can be used: Al, Si, Ce, Zr, Ti, V, Cr, Zn, Mg. The invention also encompasses the use of mixed oxides comprising two or more elements. In one embodiment of the invention mixed oxides are used as support selected from the group consisting of (Al/Si), (Mg/Si) and (Zn/Si) mixed oxides. In a preferred embodiment, an oxidic support is used, selected from the group consisting of aluminum oxide and silcium dioxide. Aluminium oxide can be employed in any phase, such as alpha aluminium oxide ($\alpha$-Al$_2$O$_3$), beta aluminium oxide (ß-Al$_2$O$_3$), gamma aluminium oxide ($\gamma$-Al$_2$O$_3$), delta aluminium oxide ($\delta$-Al$_2$O$_3$), eta aluminium oxide ($\eta$-Al$_2$O$_3$), theta aluminium oxide ($\theta$-Al$_2$O$_3$), chi aluminium oxide ($\chi$-Al$_2$O$_3$), kappa aluminium oxide ($\kappa$-Al$_2$O$_3$) and mixtures thereof. The term beta aluminium oxide (ß-Al$_2$O$_3$) describes the compound Na$_2$O.11Al$_2$O$_3$.

In a preferred embodiment, the oxidic support is selected from the group consisting of alpha aluminium oxide ($\alpha$-Al$_2$O$_3$), beta aluminium oxide (ß-Al$_2$O$_3$), gamma aluminium oxide ($\gamma$-Al$_2$O$_3$), delta aluminium oxide ($\delta$-Al$_2$O$_3$), and theta aluminium oxide ($\theta$-Al$_2$O$_3$).

In a preferred embodiment, the oxidic support is selected from the group consisting of alpha aluminium oxide ($\alpha$-Al$_2$O$_3$), beta aluminium oxide (ß-Al$_2$O$_3$) and gamma aluminium oxide ($\gamma$-Al$_2$O$_3$). In one embodiment, the oxidic support is gamma aluminium oxide ($\gamma$-Al$_2$O$_3$).

Commercially available gamma aluminium oxide ($\gamma$-Al$_2$O$_3$), can be treated at temperatures from 500 to 700° C., preferably at temperatures from 550° C. to 600° C. to ensure that the complete Al$_2$O$_3$ is in the gamma-phase.

In one embodiment the oxidic supports can have a BET-surface area (BET, Brunnauer-Emmet-Teller determined according to DIN 66131 by N$_2$ adsorption at 77 K) from 0.1 to 500 m$^2$/g. Preferably the oxidic supports have a BET-surface area of at least 0.1 m$^2$/g, preferably at least 1 m$^2$/g, preferably at least 10 m$^2$/g, more preferably of at least 30 m$^2$/g, more preferably of at least 50 m$^2$/g, more preferably of at least 75 m$^2$/g, preferably of at least 100 m$^2$/g, preferably of at least 150 m$^2$/g especially preferred of at least 200 m$^2$/g.

In a further embodiment, the oxidic support has a BET-surface area of 1 m$^2$/g to 50 m$^2$/g. In a further embodiment, the oxidic support has a BET-surface area of 10 m$^2$/g to 300 m$^2$/g, preferably of 20 to 100 m$^2$/g. In a further embodiment, the oxidic support has a BET-surface area of 100 m$^2$/g to 300 m$^2$/g, preferably 150 to 300 m$^2$/g.

In a preferred embodiment, the support is Al$_2$O$_3$ with a BET-surface area of 100 to 300 m$^2$/g.

In one embodiment, the catalyst comprises platinum on a support.

In one embodiment, the catalyst comprises platinum on a support, wherein the support is selected from carbonaceous and oxidic materials.

In one embodiment, the catalyst comprises platinum on a support, wherein the support is selected from carbonaceous and oxidic materials, and wherein the oxidic material is selected from the group consisting of oxides of the elements selected from the group consisting of Al, Ce, Zr, Ti, V, Cr, Zn and Mg.

In one embodiment, the catalyst comprises of platinum on a support, wherein the support is selected from carbonaceous materials and oxidic materials, and wherein the oxide is selected from the group consisting of oxides of the elements selected from the group consisting of Al, Ce, Zr and Ti. In a preferred embodiment, the catalyst is selected from the group consisting of platinum on carbon (Pt/C) and platinum on aluminium oxide (Pt/Al$_2$O$_3$).

In a preferred embodiment, the catalyst comprises platinum on aluminium oxide, wherein the aluminium oxide is selected from the group consisting of alpha aluminium oxide ($\alpha$-Al$_2$O$_3$), beta aluminium oxide (ß-Al$_2$O$_3$), gamma aluminium oxide (γ-Al$_2$O$_3$), delta aluminium oxide (δ-Al$_2$O$_3$), eta aluminium oxide (η-Al$_2$O$_3$), theta aluminium oxide (θ-Al$_2$O$_3$), chi aluminium oxide (χ-Al$_2$O$_3$) and kappa aluminium oxide (κ-Al$_2$O$_3$).

The content of the catalytically active metal of the catalyst usually is in the range of 0.1 to 20 weight-%, preferably 0.1 to 15 weight-%, preferably in the range of 0.5 to 10 weight-%.

The catalyst can be prepared for example by a deposition-reduction method, in which a metal compound is first deposited on a support and then reduced to the catalytically active metal. The reduction can be performed with any known method, for example in the gas phase or in the liquid phase.

In a preferred embodiment of the invention, a catalyst is used which is obtainable by
a) providing a support
b) providing a metal compound
c) depositing the metal compound on the support
d) optionally calcinating the so obtained catalyst precursor
e) reducing the catalyst precursor
f) optionally recovering the catalyst.

In a preferred embodiment of the invention, a catalyst is used which is obtained by
a) providing a support
b) providing a metal compound
c) depositing the metal compound on the support
d) optionally calcinating the so obtained catalyst precursor
e) reducing the catalyst precursor
f) optionally recovering the catalyst.

Step a) Providing a Support

A suitable support is provided, for example by adding the support in form of a powder or a shaped body directly to a reactor vessel or by providing the support as a slurry (in case the support is in form of a powder).

Step b) Providing a Metal Compound

The metal compound is a precursor of the catalytically active metal. The catalytically active metal is obtained by reduction of the metal compound.

The metal compound can be employed as solution, for example as an aqueous solution of a water-soluble salt of the metal compound or as a non-aqueous solution. The metal compound can also be employed as a colloid in which the non-dissolved metal compound is dispersed in a liquid phase.

In a preferred embodiment, the metal compound is employed as a salt. Depending on the solubility of the salt, aqueous or non-aqueous solutions can be employed.

Suitable salts of the metal compound include nitrates, acetates, sulphates, citrates, oxides, hydroxides and chlorides and combinations thereof. Preferably water-soluble salts are used.

In a preferred embodiment, the metal compound is selected from the group consisting of platinum salts. Depending on the solubility of the platinum salt, aqueous or non-aqueous solutions of the platinum salt can be employed. Examples for suitable platinum salts are H$_2$PtCl$_6$, Pt(NH$_3$)$_2$(NO$_3$)$_2$, Pt(NO$_2$)$_2$(NH$_3$)$_2$/NH$_4$OH, Pt(NO$_3$)$_2$, platinum hydroxides such as Pt(OH)$_2$, Pt(OH)$_4$, or H$_2$Pt(OH)$_6$, all of which can be stabilized in amines, for example in mono-ethanolamine, PtO$_2$, bis(2,4-pentanedionato)Platinum (II)=Pt(C$_5$H$_7$O$_2$)$_2$, K$_2$PtCl$_4$, NaPtCl$_4$, (NH$_4$)$_2$PtCl$_4$.

In a preferred embodiment, the platinum salt is selected from the group consisting of H$_2$PtCl$_6$, Pt(NH$_3$)$_2$(NO$_3$)$_2$, Pt(NO$_2$)$_2$(NH$_3$)$_2$/NH$_4$OH and Pt(NO$_3$)$_2$.

Generally, the deposition step c) will be performed prior to the reduction step e). The invention also encompasses the embodiment that the catalytically active metal can be reduced in situ from a metal compound and then deposited on the support.

In case promotors are employed, they can for example be employed as promotor compounds, which are subsequently converted (by oxidation and/or reduction) to the promotors. The promotor compound can be employed as solution, for example as an aqueous solution of a water-soluble salt of the promotor compound or as a non-aqueous solution of the promotor compound. The promotor compound can also be employed as a colloid in which the non-dissolved promotor compound is dispersed in a liquid phase.

Suitable salts of the promotor compound include nitrates, acetates, sulphates, citrates, oxides, hydroxides and chlorides and combinations thereof. Preferably water-soluble salts are used.

In case promotor compounds are employed, they can be added to the metal compound. In this embodiment, the metal compound and the promotor compound are deposited together on the support. In an alternative embodiment, the metal compound and the promotor compound can be deposited separately on the support.

After the one or more deposition step(s), both promotor compound and metal compound are then converted to promotor and catalytically active metal.

In a preferred embodiment, the promotor compound is selected from the group consisting of Bi salts, Cd salts and Pb salts.

Step c) Deposition Step

The deposition of the metal compound on the support can be performed with any known method, for example by chemical or physical vapour deposition or by contacting and mixing the support with the metal compound (=immersion) or by spraying the metal compound on the support.

In a preferred embodiment, the deposition is performed by immersion and/or spraying.

In case the deposition is performed by immersion or by spraying, the metal compound can be employed as solution or as colloid or as a colloid which is generated in situ during the immersion or spraying. The deposition by immersion or spraying can be performed at a temperature of 1 to 100° C. The pH value at which the deposition step is performed can be chosen depending on the metal compound used. The deposition can be performed from 0.1 to 24 hours, usually from 0.5 to 2 hours. The deposition can be performed at different pressures, for example at pressures from 1 to 1000 mbar (atmospheric pressure), suitable pressures are for example 50 mbar, 70 mbar, 100 mbar, 250 mbar, 500 mbar or atmospheric pressure. The so obtained catalyst precursor can optionally be dried and/or calcined prior to the reduction step.

In case the deposition step is performed by immersion or by spraying, the volume of the solution or colloid of the metal compound is ideally chosen, so that at least 90%, preferably 100% of the pore volume of the support will be filled with the solution or colloid (so called "incipient-wetness" method). The concentration of the metal compound is ideally chosen so that, after deposition and reduction, a catalyst with the desired content of catalytically active metal is obtained.

The deposition step can be conducted in one step or in multiple, consecutive steps. The deposition step can also be performed as a combination of spraying and immersion.

The catalyst precursor can then be recovered by suitable separation means such as filtration and/or centrifugation. The catalyst precursor can then be washed with water, preferably until a conductivity of less than 400 µS/cm, preferably less than 200 µS/cm is obtained.

In one embodiment, a drying step and/or a calcination step d) can be performed subsequent to the deposition step c).

The calcination step d) can be performed in customary furnaces, for example in rotary furnaces, in chamber furnaces, in tunnel furnaces or in belt calciners.

The calcination step d) can be performed at temperatures from above 200° C. to 1150° C., preferably from 250 to 900° C., preferably from 280° C. to 800° C. and more preferably from 500 to 800° C., preferably from 300° C. to 700° C. The calcination is suitably conducted for 0.5 to 20 hours, preferably from 0.5 to 10 hours, preferably from 0.5 to 5 hours.

The calcination of the catalyst precursor in step d) mainly serves the purpose to stabilize the metal compound (and if present also the promotor compound) deposited on the support and to remove undesired components.

Step e) Reduction Step

The so obtained catalyst precursor can then be reduced, for example by treatment with a gas (gas phase reduction) or by treatment of the catalyst precursor with a solution of a reducing agent (liquid phase reduction).

The gas phase reduction of the catalyst precursor can be performed by treating the catalyst precursor with hydrogen and/or CO. The hydrogen and/or CO can further comprise at least one inert gas, such as for example helium, neon or argon, $N_2$, $CO_2$ and/or lower alkanes, such as methane, ethane, propane and/or butane. Preferably $N_2$ is employed as the inert gas. The gas phase reduction can be performed at temperatures from 30° C. to 200° C., preferably from 50° C. to 180° C., more preferably from 60 to 130° C. Usually the gas phase reduction is performed over a period from 1 to 24 hours, preferably 3 to 20 hours, more preferably 6 to 14 hours.

The liquid phase reduction of the catalyst precursor is performed by treating the catalyst precursor with a solution of a reducing agent. Suitable reducing agents are quaternary alkyl ammonium salts; formic acid; salts of formic acid, such as sodium formate, potassium formate, lithium formate or ammonium formate; citric acid; salts of citric acid such as sodium citrate, potassium citrate, lithium citrate, ammonium citrate; ascorbic acid; salts of ascorbic acid such as sodium ascorbate, potassium ascorbate, lithium ascorbate and ammonium ascorbate; tartaric acid; salts of tartaric acid, such as sodium tartrate, potassium tartrate, lithium tartrate and ammonium tartrate; oxalic acid; salt of oxalic acid, such as potassium oxalate, sodium oxalate, lithium oxalate and ammonium oxalate; ammonium hydrogen carbonate ($NH_4HCO_3$); hydroxylamine; hypophosphoric acid; hypophoshites, such as for example sodium hypophosphite ($NaH_2PO_2$); sodium sulfite ($Na_2SO_3$); hydrazine; phenylhydrazine; $C_1$ to $C_4$ alcohols such methanol, ethanol, 1-propanol, 2-propanol, 1-butanol, iso-butanol (2-methyl-1-propanol), 2-butanol; diols; polyols; reducing sugars, such as glucose, fructose; borohydrides, such as $LiBH_4$, $NaBH_4$, $NaBH_3CN$, $KBH_4$, $LiBH(C_2H_5)_3$; diboran ($B_2H_6$); lithium aluminium hydride ($LiAlH_4$); formaldehyde; N-vinyl pyrrolidone (NVP), polyvinyl-pyrrolidone (PVP); phenol; sodium thiocyanate; iron(II) sulfate; sodium amalgam; zinc mercury amalgam.

The liquid phase reduction can be performed at a temperature from 10 to 95° C., preferably from 50 to 90° C. The pH of the reduction step can be chosen depending on the reducing agent used.

In a preferred embodiment, the reduction step is performed by treatment of the catalyst precursor with a solution of a reducing agent.

In a preferred embodiment, the reduction step is performed by treatment of the catalyst precursor with a solution of a reducing agent, wherein the reducing agent is selected from the group consisting of quaternary alkyl ammonium salts; formic acid; salts of formic acid, such as sodium formate, potassium formate, lithium formate or ammonium formate; citric acid; salts of citric acid such as sodium citrate, potassium citrate, lithium citrate, ammonium citrate; ascorbic acid; salts of ascorbic acid such as sodium ascorbate, potassium ascorbate, lithium ascorbate and ammonium ascorbate; tartaric acid; salts of tartaric acid, such as sodium tartrate, potassium tartrate, lithium tartrate and ammonium tartrate; oxalic acid; salt of oxalic acid, such as potassium oxalate, sodium oxalate, lithium oxalate and ammonium oxalate; ammonium hydrogen carbonate ($NH_4HCO_3$); hydroxylamine; hypophosphoric acid; hyposphoshites, such as for example sodium hypophosphite ($NaH_2PO_2$); sodium sulfite ($Na_2SO_3$); hydrazine; phenylhydrazine; $C_1$ to $C_4$ alcohols such methanol, ethanol, 1-propanol, 2-propanol, 1-butanol, iso-butanol (2-methyl-1-propanol), 2-butanol; diols; polyols; reducing sugars, such as glucose, fructose; borohydrides, such as $LiBH_4$, $NaBH_4$, $NaBH_3CN$, $KBH_4$, $LiBH(C_2H_5)_3$; diboran ($B_2H_6$); lithium aluminium hydride ($LiAlH_4$); formaldehyde; N-vinyl pyrrolidone (NVP), polyvinyl-pyrrolidone (PVP); phenol; sodium thiocyanate; iron (II) sulfate; sodium amalgam; zinc mercury amalgam.

In a preferred embodiment, the reduction step is performed by treatment of the catalyst precursor with a solution of a reducing agent, wherein the reducing agent is selected from the group consisting of sodium formate, sodium citrate, sodium ascorbate, polyols, reducing sugars, formaldehyde, methanol, ethanol and 2-propanol.

The catalyst can then be recovered by suitable separation means such as filtration and/or centrifugation. Typically, the catalyst is then washed with water, preferably until a conductivity of less than 400 µS/cm, preferably less than 200 µS/cm is obtained.

Drying steps can be performed for example subsequent to step c) and/or subsequent to step e). The drying of the catalyst precursor obtained in step c) or of the catalyst obtained in step e) can generally be performed at temperatures above 60° C., preferably above 80° C., more preferably above 100° C. The drying can for example be performed at temperatures from 120° C. up to 200° C. The drying will normally be performed until substantially all the water is evaporated. Common drying times range from one to up to 30 hours and depend on the drying temperature. The drying step can be accelerated by the use of vacuum.

The catalytically active metal can be evenly distributed on the support or can be unevenly distributed on the support. The catalytically active metal can for example be concentrated in the core or in defined layers of the support. The catalytically active metal can be located partially or completely on the inner surface of the support or can be located partially or completely on the outer surface of the support.

In case the catalytically active metal is located completely on the inner surface of the support, the outer surface of the catalyst is identical to the outer surface of the support.

The distribution of the catalytically active metal can be determined with Scanning Electron Microscopy (SEM) and Energy Dispersive X-Ray Spectroscopy (EDXS). The distribution can for example be determined by preparing a cross section of the catalyst. In case the catalyst is a sphere the cross section can be prepared through the center of the sphere. In case the catalyst is a strand, the cross section can be prepared by cutting the strand at a right angle to the axis of the strand. Via backscattered electrons (BSE) the distribution of the catalytically active metal in the catalyst can be visualized. The amount of catalytically active metal can then be quantified via EDXS whereby an acceleration voltage of 20 kV is usually used.

In a preferred embodiment of the invention a catalyst is employed, wherein the catalytically active metal is located in the outer shell of the catalyst. In this embodiment, the catalytically active metal is mainly located in the outer shell of the catalyst.

In one embodiment, the outer shell of the catalyst is the space from the outer surface of the catalyst to a depth of X from the outer surface of the catalyst, wherein X is 15% of the distance from the outer surface of the catalyst to the center of the catalyst. For example, in case a catalyst is employed which is a sphere and has a diameter of 1.5 mm, the outer shell is the space from the outer surface to a depth of 112.5 µm from the outer surface.

In one embodiment, the outer shell of the catalyst is the space from the outer surface of the catalyst to a depth of X from the outer surface of the catalyst, wherein X is 30% of the distance from the outer surface of the catalyst to the center of the catalyst. For example, in case a catalyst is employed which is a sphere and has a diameter of 1.5 mm, the outer shell is the space from the outer surface to a depth of 225 µm from the outer surface.

In one embodiment, the outer shell of the catalyst is the space from the outer surface of the catalyst to a depth of 100 µm from the outer surface of the catalyst.

In one embodiment, the outer shell is the space from the outer surface of the catalyst to a depth of 400 µm, preferably 300 µm, preferably 200 µm from the outer surface of the catalyst.

In a preferred embodiment, at least 50 weight-%, preferably at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of X from the outer surface of the catalyst, wherein X is 15% of the distance from the outer surface of the catalyst to the center of the catalyst.

In a preferred embodiment, at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of X from the outer surface of the catalyst, wherein X is 30% of the distance from the outer surface of the catalyst to the center of the catalyst.

In a further embodiment of the invention, at least 50 weight-%, preferably at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of 100 µm from the outer surface of the catalyst.

In a further embodiment of the invention, at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of 400 µm, preferably to a depth of 300 µm, preferably to a depth of 200 µm from the outer surface of the catalyst.

In a further embodiment of the invention, a catalyst is employed, wherein the dispersity of the catalytically active metal is on average in the range of 10% to 100%, preferably 30% to 95% (determined with CO-sorption according to DIN 66136-3).

Catalysts in which the catalytically active metal is located in the outer shell of the catalyst can for example be obtained by the deposition-reduction method as described above. The distribution of the catalytically active metal in the outer shell of the catalyst can be effected for example by the choice of the deposition method and/or the choice of the deposition parameters such as temperature, pH and time and the combination of these parameters. A description of the different methods of preparation can for example be found in "Handbook of Heterogeneous Catalysis", edited by G. Ertl, H. Knözinger, J. Weitkamp, Vol 1. Wiley-VCH, 1997. Chapter 2, part 2.2.1.1. Impregnation and Ion Exchange, authors M. Che, O. Clause, and Ch. Marcilly, p. 315-340.

The promotor can be evenly distributed on the support or can be unevenly distributed on the support. In a preferred embodiment, the promotor is distributed in the same way as the catalytically active material on the support.

One embodiment of the invention is directed to a process for the preparation of alpha, beta unsaturated aldehydes of general formula (I)

wherein $R_1$, $R_2$ and $R_3$, independently of one another, are selected from
hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;
by oxidation of alcohols of general formula (II)

wherein $R_1$, $R_2$ and $R_3$ have the meaning as given above in the presence of a catalyst and in the presence of a liquid phase, wherein the liquid phase contains at least 25 weight-% water based on the total weight of the liquid phase, determined at a temperature of 20° C. and a pressure of 1 bar and wherein the oxidant is oxygen, and wherein the catalyst comprises a catalytically active metal on a support and wherein at least 50 weight-%, preferably at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of X from the outer surface of the catalyst, wherein X is 15% of the distance from the outer surface of the catalyst to the center of the catalyst.

One embodiment of the invention is directed to a process for the preparation of alpha, beta unsaturated aldehydes of general formula (I)

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

(II)

wherein $R_1$, $R_2$ and $R_3$ have the meaning as given above in the presence of a catalyst and in the presence of a liquid phase, wherein the liquid phase contains at least 25 weight-% water based on the total weight of the liquid phase, determined at a temperature of 20° C. and a pressure of 1 bar and wherein the oxidant is oxygen, and wherein the catalyst comprises a catalytically active metal on a support and wherein at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of X from the outer surface of the catalyst, wherein X is 30% of the distance from the outer surface of the catalyst to the center of the catalyst.

One embodiment of the invention is directed to a process for the preparation of alpha, beta unsaturated aldehydes of general formula (I)

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

(II)

wherein $R_1$, $R_2$ and $R_3$ have the meaning as given above in the presence of a catalyst and in the presence of a liquid phase, wherein the liquid phase contains at least 25 weight-% water based on the total weight of the liquid phase, determined at a temperature of 20° C. and a pressure of 1 bar and wherein the oxidant is oxygen, and wherein the catalyst comprises a catalytically active metal on a support and wherein at least 50 weight-%, preferably at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of 100 µm from the outer surface of the catalyst.

One embodiment of the invention is directed to a process for the preparation of alpha, beta unsaturated aldehydes of general formula (I)

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;
by oxidation of alcohols of general formula (II)

(II)

wherein $R_1$, $R_2$ and $R_3$ have the meaning as given above in the presence of a catalyst and in the presence of a liquid phase,
wherein the liquid phase contains at least 25 weight-% water based on the total weight of the liquid phase, determined at a temperature of 20° C. and a pressure of 1 bar and
wherein the oxidant is oxygen, and
wherein the catalyst comprises a catalytically active metal on a support and
wherein at least 70 weight-%, preferably at least 80 weight-%, preferably at least 90 weight-%, preferably at least 95 weight-% of the catalytically active metal is located in the outer shell of the catalyst, wherein the outer shell of the catalyst is the space from the outer surface of the catalyst to a depth of 400 μm, preferably to a depth of 300 μm, preferably to a depth of 200 μm from the outer surface of the catalyst.

Process Mode

The embodiments of the process mode described hereinafter can suitably be applied in all processes described above.

The process according to the invention can be performed in reaction vessels customary for such reactions, the reaction being configurable in a continuous, semi-batch or batch-wise mode. In general, the particular reactions will be performed under atmospheric pressure. The process may, however, also be performed under reduced or increased pressure.

The process according to the invention can be performed under pressure, preferably under a pressure between above 1 bar and 15 bar (absolute), preferably between above 1 bar and 10 bar (absolute).

The process according to the invention can be performed at a partial pressure of oxygen from 0.1 to 15 bar, preferably from 0.2 to 10 bar, preferably from 0.2 to 8 bar, more preferably from 0.2 to 5 bar, more preferably from 1 to 3, preferably from 1 to 2.5, more preferably from 1.2 to 2 bar.

In a preferred embodiment of the invention the process is conducted as a batch process. In a preferred embodiment of the invention the process is conducted as a semi-batch process. In a preferred embodiment of the invention the process is conducted as a continuous process.

In a preferred embodiment of the invention the process is conducted with a fixed-bed catalyst. In case the process according to the invention is conducted with a fixed-bed catalyst, suitable fixed-bed reactors can be selected from the group consisting of trickle-bed reactors, bubble-packed reactors, multi-tubular reactors and plate reactors.

The process according to the invention can be conducted in one fixed-bed reactor or can preferably be conducted in more than one, preferably more than two, more preferably more than three, preferably three to five fixed-bed reactors. The one or more fixed-bed reactors can be arranged in series or in parallel.

The process according to the invention can be conducted at common values of weight hourly space velocity (WHSV), defined as the hourly mass flow of the process feed (in kg/h) per catalyst (in kg). The process can for example be performed at WHSV values of 1 to 20000, preferably 10 to 10000, preferably 20 to 5000, preferably 20 to 500, more preferably from 50 to 100 kg/kg/h.

The process according to the invention can be conducted in one or more fixed-bed reactor(s) with or without heat exchange. In one embodiment of the invention, the fixed-bed reactor(s) can be operated so that a constant temperature is held over one, some or all fixed-bed reactors. In one embodiment of the invention, the fixed-bed reactor(s) can be operated so that a defined temperature gradient is maintained over one, some or all fixed-bed reactors without heat addition or removal. In one embodiment of the invention, the fixed-bed reactor(s) can be operated with a temperature controlled profile, wherein a defined temperature profile is maintained over one, some or all fixed-bed reactors with internal or external heat addition or removal.

In a preferred embodiment of the invention the process is conducted in a trickle-bed reactor with a fixed-bed catalyst. In one embodiment of the invention, the process is conducted with more than one, preferably more than two, more preferably more than three trickle-bed reactors, which are arranged in series or in parallel, preferably in series. In one embodiment, the process is conducted with three to five trickle-bed reactors, which are arranged in series. In one embodiment, one or more, preferably each of the trickle-bed reactors can be provided with a liquid recycle stream.

In a preferred embodiment of the trickle-bed reactor, the components of the reaction can be inserted to the reactor concurrently, meaning that the liquid phase(s) and the gas phase comprising the oxidant oxygen, are inserted to the reactor at the same side, preferably at the top of the reactor.

In one embodiment of the invention the process is conducted in a bubble-packed reactor with a fixed-bed catalyst. In one embodiment of the invention, the process is conducted with more than one, preferably more than two, more preferably more than three bubble-packed reactors, which are arranged in series or in parallel, preferably in series. In one embodiment, the process is conducted with three to five bubble-packed reactors, which are arranged in series.

In one embodiment of the bubble-packed reactor, the components of the reaction can be inserted in the reactor concurrently, meaning that the liquid phase(s) and the gas phase comprising the oxidant oxygen, are inserted to the reactor at the same side, preferably at the bottom of the reactor. In one embodiment of the bubble-packed reactor, the components of the reaction can be inserted in the reactor countercurrently, meaning that the liquid phase(s) and the gas phase comprising the oxidant oxygen, are inserted to the reactor at opposite sides. In one embodiment, the liquid phase(s) are inserted to the reactor at the bottom of the reactor, whereas the gas phase comprising oxygen as oxidant is inserted at the top of the reactor. In one embodiment, the liquid phase(s) are inserted to the reactor at the top of the reactor, whereas the gas phase comprising oxygen as oxidant is inserted at the bottom of the reactor.

In a preferred embodiment of the invention the process is conducted as a slurry process. The process can be conducted in a slurry-based system as stirred tank reactor or slurry bubble column.

The reaction is carried out by contacting alcohol(s) of general formula (II), water, catalyst, the oxidant and optional components, such as for example one or more solvent(s), under suitable reaction conditions.

These components can in principle be contacted with one another in any desired sequence. For example, the alcohol(s) of general formula (II), if appropriate dissolved in water or a solvent or in dispersed form, can be initially charged and admixed with the catalyst or, conversely, the catalytic system can be initially charged and admixed with the alcohol(s) of general formula (II) and water. Alternatively, these components can also be added simultaneously to the reaction vessel.

As an example for a batch-wise slurry process a stirred tank reactor can be used where the catalyst, the reactant, water, and optionally solvent are loaded, the reactor is then pressurized with oxygen. The reaction is then performed until the desired conversion is achieved.

As an example for a batch-wise slurry process a stirred tank reactor can be used where the catalyst, the reactant(s), if appropriate dissolved in water or solvent or in dispersed form, water and optionally one or more solvent(s) are loaded, the reactor is then pressurized with oxygen. The reaction is then performed until the desired conversion is achieved.

As an example for a semi-batch process a stirred tank reactor can be used where the catalyst, the reactant(s), water, and optionally solvent are loaded, the oxygen is then continuously fed to the reactor until the desired conversion is achieved. As another example for a semi-batch process a fixed bed catalyst in a trickle-bed reactor can be used. The solution of reactant(s), water, optionally comprising solvent, are then pumped in a loop over the catalyst, oxygen is passed as a continuous stream through the reactor. In one embodiment of the invention the oxygen can be added in excess, the excess being released to the off gas, alternatively the oxygen can be added in an amount required to replenish the consumed oxygen.

As an example for a continuous slurry process, a continuous stirred tank reactor can be used in which the catalyst is present. The solution of the reactant(s), water, optionally comprising solvent and the oxidant are added continuously. Oxygen can be added in excess, off-gas can then be taken out continuously. In an alternative embodiment, oxygen can be added in an amount to replenish the consumed oxygen. The liquid reaction product can be taken off continuously through a filter in order to keep the catalyst in the reactor.

In a further example for a continuous fixed bed process, both the solution of reactant(s) and the oxidant are continuously fed to a trickle bed reactor containing the catalyst. In this case, it is possible to partly or fully recycle the gas and/or the liquid back to the reactor in order to achieve the desired conversion of reactant(s) and/or oxygen.

In a preferred embodiment, the process according to the invention is carried out in a continuous mode.

It has surprisingly been found that the process of the invention leads to selectivities of the alpha, beta unsaturated aldehyde (based on the alcohol of general formula (II)) in the range of over 90%, preferably over 93%, preferably over 95%, preferably over 97% more preferably over 99%.

Preferably the process according to the invention is conducted until a conversion of the alcohol of general formula (II) in the range of 10 to 99.99%, preferably in the range of 30 to 95%, and most preferably in the range of 50 to 80% is obtained.

Preferably the process according to the invention is performed at a temperature in the range from 1 to 250° C., preferably in the range from 5 to 150° C., preferably in the range from 20 to 100° C., more preferably in the range from 25° C. to 80° C., preferably in the range from 30 to 70° C. and more preferably in the range of 35 to 50° C. In one embodiment of the invention, the process is performed at a temperature in the range of 40 to 80° C.

The obtained crude product may be subjected to conventional purification measures, including distillation or chromatography or combined measures. Suitable distillation devices for the purification of the compounds of formula (I) include, for example, distillation columns, such as tray columns optionally equipped with bubble cap trays, sieve plates, sieve trays, packages or filler materials, or spinning band columns, such as thin film evaporators, falling film evaporators, forced circulation evaporators, wiped-film (Sambay) evaporators, etc. and combinations thereof.

Examples—Catalyst Preparation

Example C1

Step a): Support: 50 g of aluminium oxide (gamma-$Al_2O_3$ strands with a mean diameter of 1.5 mm (commercially available from Exacer s. r. l. Italy), was heated to 550° C. for 4 hours and maintained at 550° C. for 1 hour.

Step b): 6.68 g of a 15.4 wt. % $Pt(NO_3)_2$ solution in 10 weight % nitric acid and 1.29 g of $Bi(NO_3)_3$ were added to 95.21 g water at room temperature.

Step c): A flask was equipped with 50 g of aluminium oxide obtained in step a) and immersed with the Pt/Bi solution obtained in step b) and stirred for 0.5 hours at 70 mbar while the mixture was heated to 80° C. At 80° C. the solvent was removed within 30 minutes.

Drying was performed in a rotary evaporator for 60 minutes at 80° C.

Step d): The so obtained catalyst precursor was placed in a muffle furnace and heated to 450° C. over a time period of 5 hours. The temperature of 450° C. was maintained for 1 hour.

Step e): Reduction of the catalyst precursor was performed by treatment of the catalyst precursor with a solution of a reducing agent. 50 g of the catalyst precursor obtained in step d) were added to 400 g of water and heated to 60° C. An aqueous sodium formate solution was prepared (34.87 g of sodium formate (97%) plus 88.38 g water) and added dropwise to the catalyst precursor over a time period of 10 minutes. The reaction mixture was maintained at 60° C. for 140 minutes and then left to cool to room temperature under $N_2$.

The catalyst was recovered by filtration and washed with water to a conductivity below 170 µS/cm and subsequently dried at 80° C. for 4 hours.

The so obtained catalyst displayed a Pt content of 1.4 weight % and a molar ratio of Pt:Bi of 1:0.5. The distribution of the catalytically active metal Pt was determined with SEM-EDXS in a cross section of the strands: the majority of the Pt was located within 100 µm from the outer surface of the catalyst.

Example C2

Example C1 was repeated, with the following modification of step c):

Step c): A flask was equipped with 50 g of aluminium oxide obtained in step a) and immersed with the Pt/Bi solution obtained in step b) and stirred for 10 minutes at 70 mbar. The catalyst precursor was recovered by filtration.

The so obtained catalyst displayed a Pt content of 1.4 weight % and a molar ratio of Pt:Bi of 1:0.5. The distribution of the catalytically active metal Pt was determined with SEM-EDXS in a cross section of the strands: the majority of the Pt was located within 100 μm from the outer surface of the catalyst.

Example C3

Step a): Support: 50 g of aluminium oxide (gamma $Al_2O_3$ strands with a diameter of 1.5 mm (commercially available from Exacer s. r. l. Italy) was heated to 550° C. for 4 hours and maintained at 550° C. for 1 hour.

Step b): 6.63 g of a 15.4 weight % $Pt(NO_3)_2$ solution in 10 weight % nitric acid and 5.09 g of $Bi(NO_3)_3$ were added to 29.6 g water at room temperature.

Step c): A flask was equipped with 50 g of aluminium oxide obtained in step a) and rotated at 70 mbar. The Pt/Bi solution obtained in step b) was added via a dropping funnel to the injection nozzle and sprayed onto the support. The deposition step was conducted under mixing for 30 minutes at room temperature. Drying was performed in the rotary evaporator for 60 minutes at 80° C.

Step d): The so obtained catalyst precursor was placed in a muffle furnace and heated to 450° C. over a time period of 5 hours. The temperature of 450° C. was maintained for 1 hour.

Step e): Reduction of the catalyst precursor was performed by treatment of the catalyst precursor with a solution of a reducing agent. 50 g of the catalyst precursor were added to 400 g of water and heated to 60° C. An aqueous sodium formate solution was prepared (34.87 g of sodium formate (97%) plus 88.38 g water) and added dropwise to the catalyst precursor over a time period of 15 minutes. The reaction mixture was maintained at 60° C. for 120 minutes and then left to cool to room temperature under $N_2$.

The catalyst was recovered by filtration and washed with water to a conductivity below 170 μS/cm and subsequently dried at 80° C. for 4 hours.

The so obtained catalyst displayed a Pt content of 1.6 weight % and a molar ratio of Pt:Bi of 1:2.

The distribution of the catalytically active metal Pt was determined with SEM-EDXS in a cross section of the strands: the majority of the Pt was located within 100 μm from the outer surface of the catalyst.

Example C4

Example C3 was repeated, with the following modification in step b): 2.55 g (instead of 5.09 g) of $Bi(NO_3)_3$ were added to the solution.

The so obtained catalyst displayed a Pt content of 1.6 weight % and a molar ratio of Pt:Bi of 1:1. The distribution of the catalytically active metal Pt was determined with SEM-EDXS in a cross section of the strands: the majority of the Pt was located within 100 μm from the outer surface of the catalyst.

Example C5

Example C3 was repeated, with the following modification in step b): 1.27 g (instead of 5.09 g) of $Bi(NO_3)_3$ were added to the solution.

The so obtained catalyst displayed a Pt content of 1.6 weight % and a molar ratio of Pt:Bi of 1:0.5. The distribution of the catalytically active metal Pt was determined with SEM-EDXS in a cross section of the strands: the majority of the Pt was located within 400 μm from the outer surface of the catalyst.

Example C6

Step a): 40 g of gamma-aluminium oxide (strands with a diameter of 1.5 mm) was heated to 550° C. for 4 hours and maintained at 550° C. for 1 hour.

Step b): A 15.7 wt. % $Pt(NO_3)_2$ solution in 10 weight % nitric acid was prepared.

Step c): A rotary plate was equipped with 40 g of aluminium oxide obtained in step a), rotated and heated to 100° C. 15.95 g of a 15.7 wt. % $Pt(NO_3)_2$ solution in 10 weight % nitric acid was sprayed onto the support with an injection nozzle within 1 hour and 6 minutes. After the addition was complete the mixture was rotated for an additional 10 minutes on the hot rotary plate and subsequently dried.

Step d): The so obtained catalyst precursor was placed in a muffle furnace and heated to 450° C. over a time period of 3 hours. The temperature of 450° C. was maintained for 1 hour.

Step e): Reduction of the catalyst precursor was performed by treatment of the catalyst precursor with a solution of a reducing agent. 41.97 g of the catalyst precursor was added to 399.94 g of water and heated to 60° C. An aqueous sodium formate solution was prepared (29.32 g of sodium formate plus 74.13 g water) and added dropwise to the catalyst precursor over a time period of 15 minutes. The reaction mixture was maintained at 60° C. for 120 minutes and then left to cool to room temperature under $N_2$.

The catalyst was recovered by filtration and washed with water to a conductivity below 132.5 μS/cm and subsequently dried at 80° C. for 4.5 hours.

The so obtained catalyst displayed Pt content of 2.6 weight %. The distribution of the catalytically active metal Pt was determined with SEM-EDXS in a cross section of the strands: the majority of the Pt was located within 100 μm from the surface of the catalyst.

The invention claimed is:

1. A process for the preparation of alpha, beta unsaturated aldehydes of general formula (I)

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

(II)

wherein $R_1$, $R_2$ and $R_3$ have the meaning as given above in the presence of a catalyst and in the presence of a liquid phase, wherein the liquid phase contains at least 25 weight-% water based on the total weight of the liquid phase, determined at a temperature of 20° C. and a pressure of 1 bar and wherein the oxidant is oxygen, and wherein the catalyst comprises a catalytically active metal on a support and the catalytically active metal is located mainly in the outer shell of the catalyst, wherein the outer shell of the catalyst is the space from the outer surface of the catalyst to a depth of X from the outer surface of the catalyst, wherein X is 15 % of the distance from the outer surface of the catalyst to the center of the catalyst.

2. A process for the preparation of alpha, beta unsaturated aldehydes of general formula (I)

(I)

wherein $R_1$, $R_2$ and $R_3$, independently of one another, are selected from hydrogen; $C_1$-$C_6$-alkyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl; and $C_2$-$C_6$-alkenyl, which optionally carry 1, 2, 3, or 4 identical or different substituents which are selected from $NO_2$, CN, halogen, $C_1$-$C_6$ alkoxy, ($C_1$-$C_6$-alkoxy) carbonyl, $C_1$-$C_6$ acyl, $C_1$-$C_6$ acyloxy and aryl;

by oxidation of alcohols of general formula (II)

(II)

wherein $R_1$, $R_2$ and $R_3$ have the meaning as given above in the presence of a catalyst and in the presence of a liquid phase, wherein the liquid phase contains at least 25 weight-% water based on the total weight of the liquid phase, determined at a temperature of 20° C. and a pressure of 1 bar and wherein the oxidant is oxygen, and wherein a catalyst is used which is obtainable by
a) providing a support
b) providing a metal compound
c) depositing the metal compound on the support
d) optionally calcinating the so obtained catalyst precursor
e) reducing the catalyst precursor, by treatment of the catalyst precursor with a solution of a reducing agent
f) optionally recovering the catalyst.

3. The process according to claim 1, wherein an alcohol according to formula (II) is used, wherein $R_1$, $R_2$ or $R_3$, independently of one another, are selected from H and $CH_3$.

4. The process according to claim 1, wherein an alcohol according to formula (II) is used, wherein $R_3$ is H and $R_2$ and $R_1$ are $CH_3$.

5. The process according to claim 1, wherein the liquid phase contains at least 50 weight-%, water based on the total weight of the liquid phase.

6. The process according to claim 1, wherein the oxidation is carried out at a temperature of 20° C. to 100° C.

7. The process according to claim 1, wherein the oxidation is carried out under a partial pressure of oxygen between 0.2 and 8 bar.

8. The process according to claim 1, wherein the catalytically active metal is selected from elements selected from the group consisting of platinum, palladium and gold.

9. The process according to claim 1, wherein the support is selected from the group consisting of carbonaceous materials and oxidic materials.

10. The process according to claim 1, wherein the support is selected from the group consisting of alpha aluminium oxide ($\alpha$-$Al_2O_3$), beta aluminium oxide ($\beta$-$Al_2O_3$) and gamma aluminium oxide ($\gamma$-$Al_2O_3$).

11. The process according to claim 2, wherein an alcohol according to formula (II) is used, wherein $R_1$, $R_2$ or $R_3$, independently of one another, are selected from H and $CH_3$.

12. The process according to claim 2, wherein an alcohol according to formula (II) is used, wherein $R_3$ is H and $R_2$ and $R_1$ are $CH_3$.

13. The process according to claim 2, wherein the liquid phase contains at least 50 weight-% water based on the total weight of the liquid phase.

14. The process according to claim 2, wherein the oxidation is carried out at a temperature of 20° C. to 100° C.

15. The process according to claim 2, wherein the oxidation is carried out under a partial pressure of oxygen between 0.2 and 8 bar.

16. The process according to claim 2, wherein the catalytically active metal is selected from elements selected from the group consisting of platinum, palladium and gold.

17. The process according to claim 2, wherein the support is selected from the group consisting of carbonaceous materials and oxidic materials.

18. The process according to claim 2, wherein the support is selected from the group consisting of alpha aluminium oxide ($\alpha$-$Al_2O_3$), beta aluminium oxide ($\beta$-$Al_2O_3$) and gamma aluminium oxide ($\gamma$-$Al_2O_3$).

19. The process according to claim 1, wherein the liquid phase contains at least 70 weight-% water based on the total weight of the liquid phase and the oxidation is carried out at a temperature of 20° C. to 70° C.

20. The process according to claim 2, wherein the liquid phase contains at least 70 weight-% water based on the total weight of the liquid phase and the oxidation is carried out at a temperature of 20° C. to 70° C.

21. The process according to claim 1, wherein the outer shell of the catalyst is the space from the outer surface of the catalyst to a depth of X from the outer surface of the catalyst, wherein X is 30 % of the distance from the outer surface of the catalyst to the center of the catalyst.

22. The process according to claim 2, wherein the liquid phase contains at least 95 weight-% water based on the total weight of the liquid phase.

23. The process according to claim 2, wherein the catalyst comprises Pt and Bi.

* * * * *